(12) United States Patent
Jaeger et al.

(10) Patent No.: US 10,465,156 B2
(45) Date of Patent: Nov. 5, 2019

(54) CAP FOR CELL CULTURE CONTAINERS

(71) Applicant: HAMILTON Bonaduz AG, Bonaduz (CH)

(72) Inventors: Thomas Jaeger, Bonaduz (CH); Carsten Etzold, Bonaduz (CH); Rene Demarmels, Malans (CH)

(73) Assignee: Hamilton Bonaduz AG (CH)

( * ) Notice: Subject to any disclaimer, the term of this patent is extended or adjusted under 35 U.S.C. 154(b) by 300 days.

(21) Appl. No.: 15/031,775

(22) PCT Filed: Oct. 29, 2014

(86) PCT No.: PCT/EP2014/073197
§ 371 (c)(1),
(2) Date: Apr. 25, 2016

(87) PCT Pub. No.: WO2015/063136
PCT Pub. Date: May 7, 2015

(65) Prior Publication Data
US 2016/0244708 A1    Aug. 25, 2016

(30) Foreign Application Priority Data
Oct. 31, 2013  (DE) .................. 10 2013 112 049

(51) Int. Cl.
| C12M 1/00 | (2006.01) |
|---|---|
| C12M 1/12 | (2006.01) |
| C12M 1/34 | (2006.01) |
| F16K 21/00 | (2006.01) |
| F16K 31/02 | (2006.01) |

(52) U.S. Cl.
CPC ............ *C12M 23/38* (2013.01); *C12M 23/40* (2013.01); *C12M 29/00* (2013.01); *C12M 37/00* (2013.01); *C12M 41/00* (2013.01); *C12M 41/40* (2013.01)

(58) Field of Classification Search
CPC ....................................... C12M 23/28
USPC ....................................... 435/304.1
See application file for complete search history.

(56) References Cited

U.S. PATENT DOCUMENTS

| 4,651,574 A | 3/1987 | Spencer |
|---|---|---|
| 4,823,623 A | 4/1989 | Carpenter et al. |
| 4,887,472 A | 12/1989 | Jansen |
| 5,848,622 A | 12/1998 | Kilcoin |

(Continued)

FOREIGN PATENT DOCUMENTS

| CN | 102941962 A | 2/2013 |
|---|---|---|
| DE | 4207346 A1 | 9/1993 |

(Continued)

*Primary Examiner* — Kevin Joyner
*Assistant Examiner* — Holly M Mull
(74) *Attorney, Agent, or Firm* — Jansson Munger McKinley & Kirby Ltd.

(57) ABSTRACT

A cap for cell culture container enclosing a culture volume and having an opening, comprising a valve arrangement, suitable for filling of the cell culture container with a fluid and/or for pumping fluid out from the cell culture container, and a compensation opening suitable for aerating the cell culture container and/or for pressure compensation during filling and pumping out, said valve arrangement being designed to be switchable between an outlet position and a blocking position, to be connectable to a fluid supply interface, and to be switchable without contact.

11 Claims, 4 Drawing Sheets

(56) References Cited

U.S. PATENT DOCUMENTS

| | | |
|---|---|---|
| 2002/0086418 A1 | 7/2002 | Powell |
| 2004/0101445 A1* | 5/2004 | Shvets .................. B01L 3/0265 |
| | | 422/521 |
| 2005/0109974 A1* | 5/2005 | Antunes Guimaraes ..................... |
| | | F16K 1/08 |
| | | 251/357 |
| 2009/0152744 A1 | 6/2009 | Mou |
| 2012/0248111 A1 | 10/2012 | Bear et al. |
| 2013/0064738 A1* | 3/2013 | Berger ..................... B01J 4/002 |
| | | 422/521 |
| 2013/0078708 A1* | 3/2013 | Roux Dit Buisson ....................... |
| | | C12M 21/02 |
| | | 435/257.1 |
| 2018/0023121 A1* | 1/2018 | Niemz ................ B01L 3/50273 |

FOREIGN PATENT DOCUMENTS

| | | |
|---|---|---|
| EP | 1591517 | 11/2005 |
| EP | 2251407 | 11/2010 |

\* cited by examiner

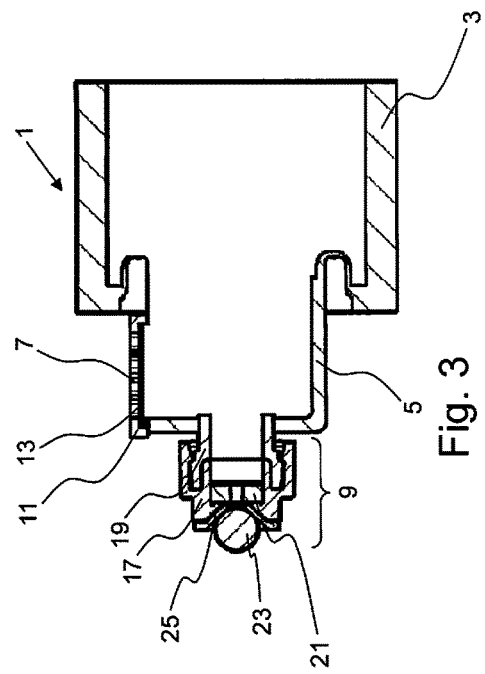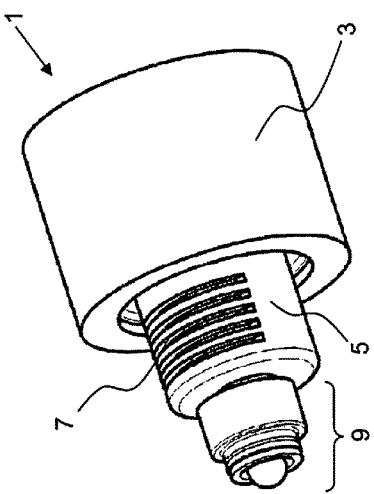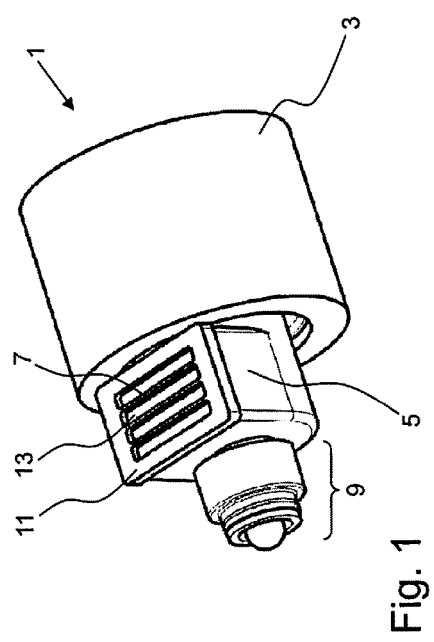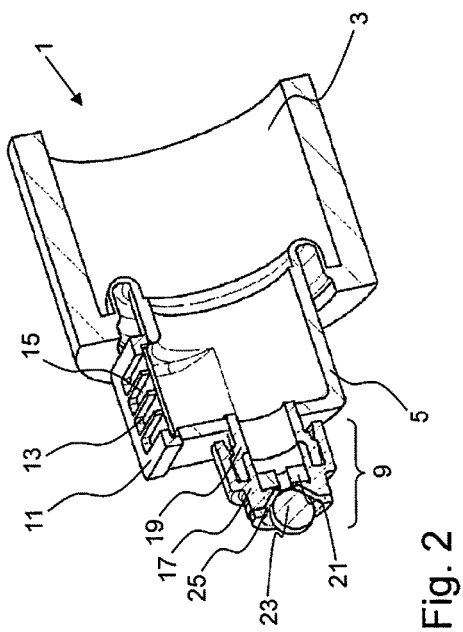

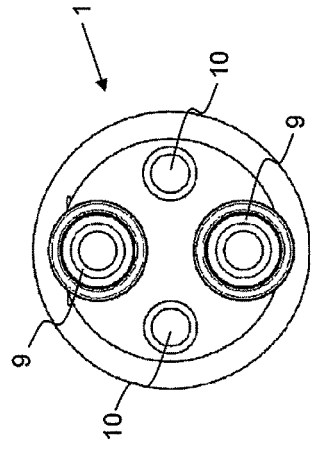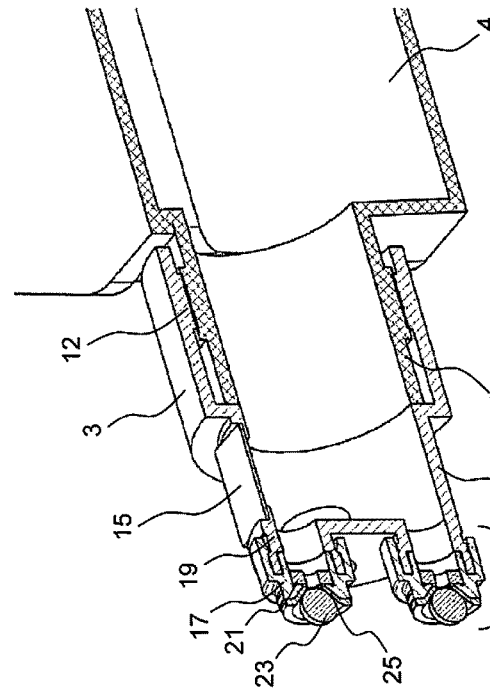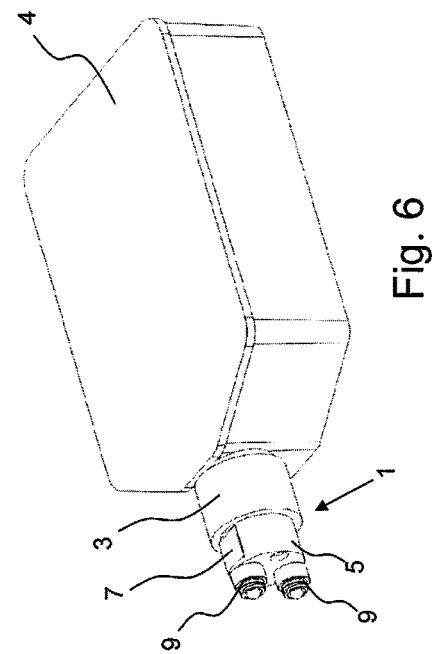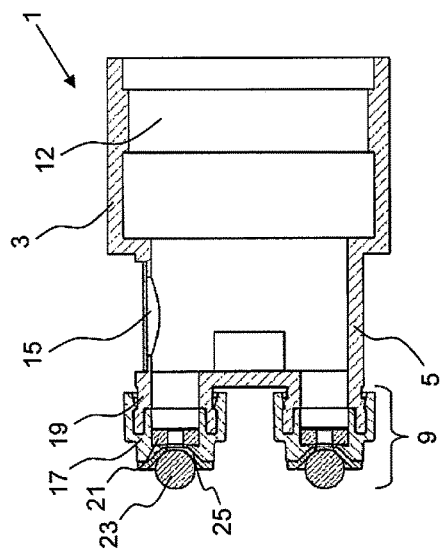

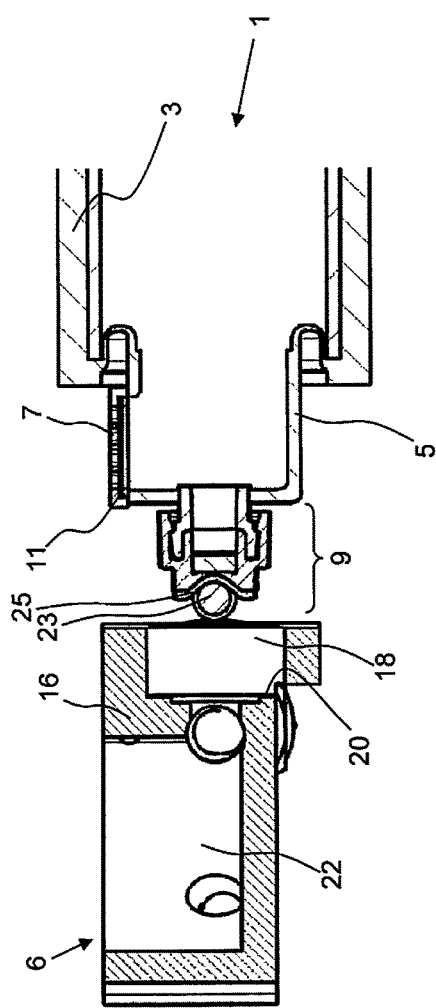
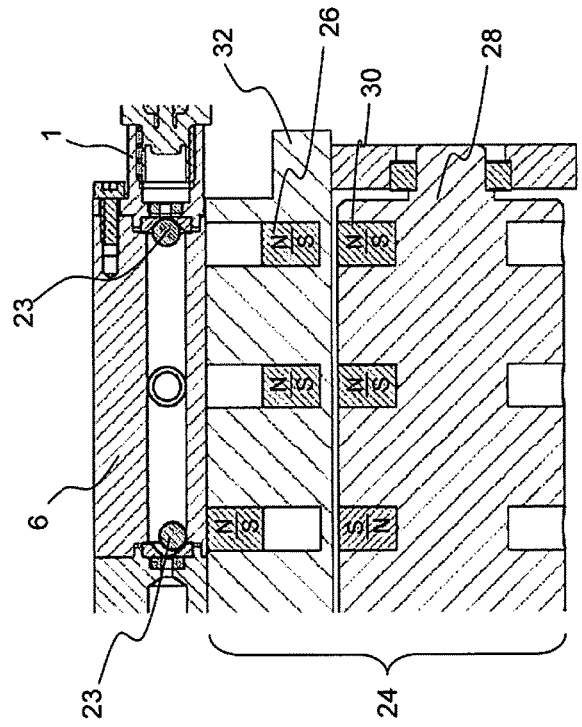
Fig. 10
Fig. 11

CAP FOR CELL CULTURE CONTAINERS

FIELD OF THE INVENTION

The present invention pertains to a cap for cell culture containers such as those usually used for the industrial cultivation of adherent cells in laboratories of the pharmaceutical and biotechnology industries.

BACKGROUND OF THE INVENTION

In the field of cell culture, cell culture containers are known which are usually made of transparent plastic, frequently as disposable or single-use containers, and which have one or more screw caps. The cell culture containers are used to propagate cells, i.e., to cultivate them, and to observe their growth. For this purpose, the cells to be cultivated are added together with a suitable nutrient medium to the container (often in the form of a bottle), where they can grow under appropriate environmental conditions. The interior of the cell culture container comprises a certain volume, which for this reason is called the culture volume. The environmental conditions usually consist of an ambient temperature of 37° C. with a $CO_2$ content of 5% and a relative humidity (rH) of 95%. As soon as a certain percentage of the surface of the cell culture container is covered with the adherent cells (degree of confluence), the cells must either be harvested for further use or distributed over several new cell culture containers. In many cases, it is also necessary to renew the nutrient medium during cultivation (cell maintenance). For the replacement of the nutrient medium and/or the removal of adherent cells, possibly with or without nutrient medium, the term "fluid" is used here in a comprehensive sense.

For small quantities of cells to be cultivated, i.e., in the simplest case, the above-mentioned steps in the cell culture process are performed manually by appropriately trained technical assistants with the help of hand pipettes under a sterile laboratory hood. That is, the caps of the cell culture containers are unscrewed by hand, and, after the fluid has been added or removed, they are screwed back on by hand. Specially made, dedicated shaking machines and other laboratory equipment are already replacing substeps of the overall process, so that not all of the activities in question have to be carried out manually.

For larger quantities of cell cultures, fully automated solutions are available on the market, which perform all of the necessary steps by means of mechanical robots such as, for example, the 6-axis robots made by TAP and Kawasaki. With these robot solutions, the same cell culture containers as those used for manual processing can be used, which eliminates the cost of buying new cell culture containers. The disadvantage of the automated robot solutions, however, is that the throughput and the speed of processing is very limited, and it is very difficult if not impossible to carry out the steps of the process in parallel or in an interleaved manner.

The cell culture containers currently in use have screw-on caps or covers, which can be configured as desired with or without a vent membrane to ensure efficient $CO_2$ exchange with the cells inside the bottle. An important aspect of these aerating or filter membranes is that the pore size of the membrane may not exceed 0.22 µm, because otherwise the membrane could not still be considered a sterile membrane.

There are also various special forms of cell culture containers with pierceable membranes configured to serve as, for example, hydrophobic filter membranes; an example of such a special container is the cell culture bottle "Auto-Flask" sold by the company Greiner Bio-One. These types of cell culture containers are optimized for automated processes, are compatible with a large number of different cell culture systems and liquid handling systems, and comprise, for example, a physical surface treatment for adherent cells. The disadvantage of these products, however, is that the user is limited to containers of precisely the right shape, size, and surface properties. For this reason, systems of this type are so far not in widespread use.

German patent application DE 10 2013 201 069 of the applicant is directed toward a cell culture system with a fluid supply interface and a cell culture container specially conceived for it, wherein the cell culture container comprises a filling and/or vent opening and at least one coupling formation configured separately from the filling and/or vent opening, this coupling formation being configured in such a way that the container can be attached to and detached from a corresponding coupling formation of the fluid supply interface. This cell culture system, i.e., this cell culture container, is therefore also adapted specifically to the corresponding system or interface, for which reason only some or only very few of the standard cell culture containers used in the past are still usable. To equip an entire laboratory or production facility with these new cell culture containers therefore requires a very large investment.

It is therefore the object of the present invention to provide a technical teaching for a cap of a cell culture container, wherein the cap not only overcomes the disadvantages described above but is also usable with the standard cell culture containers used in the past, is producible at low cost, and comprises a simple structure.

SUMMARY OF THE INVENTION

According to one aspect of the invention, a cap for a cell culture container is provided, which encloses a culture volume and has an opening, the cap comprising a valve arrangement suitable for filling the cell culture container with a fluid and/or for pumping fluid out from the cell culture container, and a compensation opening suitable for aerating the cell culture container and/or for to pressure compensation during filling or pumping out, said valve arrangement being designed to be switchable between an outlet position and a blocking position, to be connectable to a fluid supply interface, and to be switchable without contact. By integrating the valve arrangement into the cover or cap, already existing cell culture containers can be easily used in an automated cell culture system. The conversion from manual processing to an essentially automatic cell culture system thus requires only the investment in new caps for the cell culture containers already on hand. Because of the compensation opening integrated into the cover or cap, there is no longer any need for an additional opening in the cell culture container. Proper $CO_2$ exchange is thus ensured. In addition, this also ensures a sufficient volume flow rate during filling or emptying of the cell culture container. The structure of the cap, furthermore, is simple, and it can be produced at low cost, especially in comparison to the specialized production of an entire cell culture container for use in an automated cell culture system.

Because the valve arrangement is configured to be switchable without contact, automated cell culture systems or machines can easily make use of cell culture containers equipped with the cap according to the invention. The contactless switchability means that the structure is simple and enables an especially easy handling, because no cables or other lines need to be connected to the cap to cause the valve arrangement to open or close. This makes it possible in particular to clean an automated cell culture system easily, in contrast to systems with switching mechanisms for the valve arrangements which require contact to open and close them; because of their complicated structure, such systems can be cleaned only with considerable effort.

According to a preferred aspect of the invention the compensation opening can be configured, selectively, either as an opening which can be opened and closed and/or as a membrane. Thus the compensation opening can be opened or closed during the filling or emptying process, depending on whether the volume flow rate is to be increased or decreased. The configuration as a membrane, preferably a hydrophobic membrane, is important for the $CO_2$ exchange in the rest state, that is, the state in which no removal, filling, or pumping-out is taking place. The compensation opening such as a membrane of this type can also be protected from damage by a grating, for example, without causing any interference with its function. If the cap is essentially cylindrical in shape, the compensation opening can be arranged on the lateral surface or on the end surface of the cap.

It is especially preferred that the valve arrangement and the opening of the cell culture container be arranged coaxially. In the case of a cylindrical cap, therefore, the valve arrangement will be located essentially in the center of the end face of the cap, i.e., on an extension of the common axis. When this arrangement is selected, it is more advantageous for the compensation opening to be arranged on the lateral surface.

It is also advantageous for the compensation opening to be configured in such a way that it is closed when the valve arrangement is not connected to the fluid supply interface and that it is open when the valve arrangement is connected to the fluid supply interface. This represents a "docking" function, according to which the compensation opening does not open until the valve arrangement of the cap has been installed in the opposing piece, that is, in the port of the fluid supply interface. For example, this can be done by means of a mechanical slider mechanism comprising a return spring.

It is advantageous for the cap to be detachably connectable to the opening of the cell culture container by means of a threaded joint, a bayonet lock connection, a press-fit connection, a snap-on or plug-in connection, or a combination of these possibilities. The connection by means of a thread, i.e., the standard screw-on connection, will be the type of connection used most often, because the cell culture containers used up to now have an opening with a screw thread. It is to be noted here that the connection in question can also be provided with seals or gaskets.

It is especially advantageous for the valve arrangement to comprise a magnetic ball-type valve, wherein a magnetic element on the valve seat is arranged on the side of the valve arrangement facing the container and a ball of magnetic material is arranged on the side of the valve arrangement facing away from the container. The magnetic ball valve offers the advantage that it takes up very little surface area and has a simple structure; in addition, the side of the cap with the ball facing away from the container can be cleaned relatively easily, which thus fulfills one of the essential requirements on an automated cell culture system, namely, that contamination of the cell cultures must be reduced to the lowest possible level. As will be described in greater detail below, the ball-type valve is controlled by the control unit inside the fluid supply interface. In the closed state, the magnetic forces of the ball and the magnetic element on the valve seat act in such a way that the corresponding elements attract each other and thus hold the ball relatively firmly on the valve seat, thus preventing fluid from flowing into the cell culture container or out of it. The magnetic elements actuated by the control unit in the fluid supply interface are, in the docked state, arranged near the ball in such a way and are of such a size that actuating these magnetic elements generates a magnetic field capable of moving the ball out of its closed position, thus releasing a path through which the fluid can flow.

The valve seat is preferably conical or hemispherical. Thus the ball is effectively held on the valve seat in the closed state and can be moved away from it only by a force which exceeds a certain minimum. In principle, however, it is also possible for the valve seat to be flat. Cleaning can then be carried out very effectively, because the cleaning liquid can reach the intermediate spaces more easily.

It is advantageous for the valve seat to be made of a thermoplastic plastic material such as thermoplastic elastomers (TPE), silicone, or the like, wherein the thermoplastic material preferably comprises a Shore A hardness of approximately 25 to approximately 50. Materials of this type give the valve seat an essentially easy-to-deform property and thus improve the sealing action of the valve arrangement. It is also possible for the valve seat to be produced out of different materials by means of two-component injection molding.

The cap, with the exception of the valve arrangement, may be produced as a one-piece unit out of plastic by injection-molding, after which the valve arrangement is attachable to it with a press fit. Injection molding is a proven, technically mature, and very low-cost production method for the plastics in question such as PP, PE, PVC, and the like. A simple structure is present, since the valve arrangement can easily be fitted onto the cap. As an option, individual components of the valve arrangement (in the case of the embodiment as a magnetic ball-type valve, all such components except for the magnetic ball and the magnetic element) can also be produced out of plastic by injection molding, possibly again by injection molding of two or more components. These can be easily assembled with the other components and the cap element to obtain the complete cap according to the invention. It is therefore also possible to realize the cap as a single-use/disposable item, which eliminates the work required to process the cap for reuse.

It is also advantageous for the cap to comprise an additional valve arrangement to serve as the compensation opening. Instead of providing the cap with its own "simple" compensation opening, an additional valve arrangement can take over this function. A siphon, for example, can be used to separate the two valve arrangements.

It is also possible to arrange several valve arrangements in the cap, preferably next to each other. Thus it is possible to fulfill even more effectively the requirements on purity and/or the avoidance of contamination, e.g., in that one valve arrangement is used only to introduce material, whereas the other valve arrangement is used only to pump it or conduct it out.

BRIEF DESCRIPTION OF THE DRAWINGS

The invention is explained in detail in the following with reference of the exemplary embodiments illustrated in the drawings:

FIG. 1 shows a perspective view of a preferred embodiment of the cap according to the invention for a cell culture container;

FIG. 2 shows a cross-sectional view, in perspective, of a preferred embodiment of the cap according to the invention of FIG. 1;

FIG. 3 shows a cross-sectional view of the cap of FIG. 1;

FIG. 4 shows a perspective view of a second embodiment of a preferred embodiment of the cap according to the invention;

FIG. 6 shows a perspective view of a cell culture container with a cap according to another embodiment of the present invention;

FIG. 7 shows a front view of the cap of FIG. 6;

FIG. 8 shows a cross-sectional view of a cap according to the additional embodiment of the present invention shown in FIGS. 6 and 7;

FIG. 9 shows a detail of a cross-sectional view, in perspective, of the cap shown in FIG. 6 with the cell culture container;

FIG. 10 shows a cross-sectional view of a detail of the diagram of FIG. 5; and

FIG. 11 shows a schematic diagram, which explains by way of example the interaction between the cap and a cell culture system according to a preferred embodiment of the invention.

DETAILED DESCRIPTION

Figure 5:
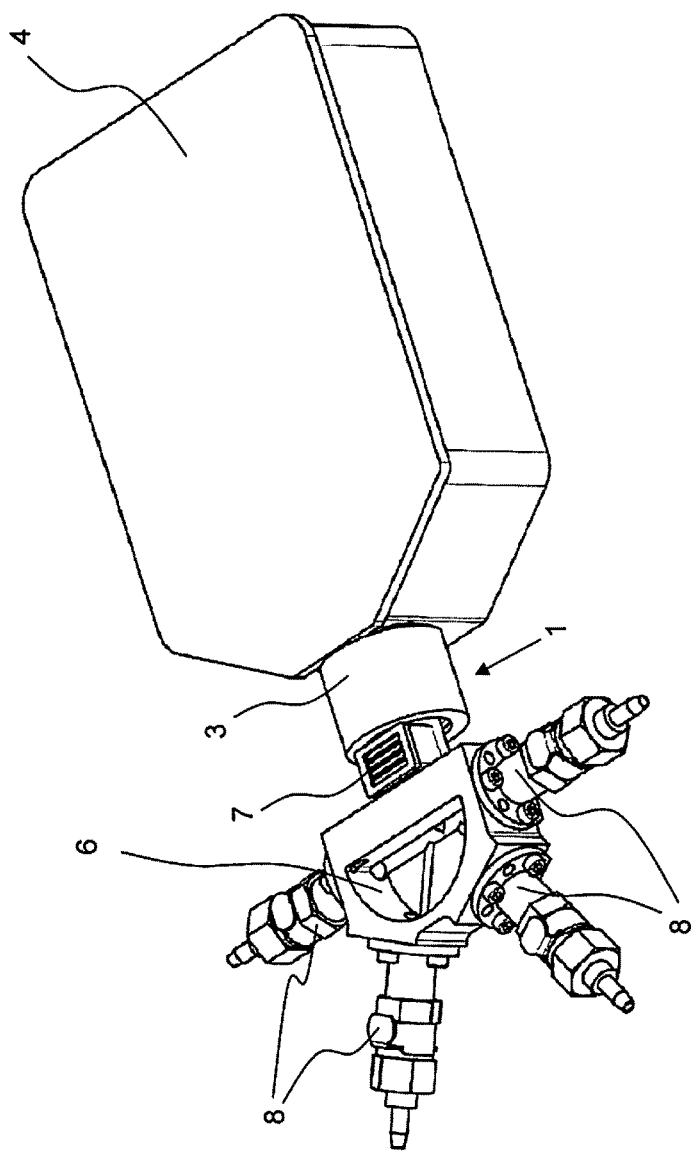
FIG. 5 shows a cap according to the first embodiment, mounted on a cell culture container and docked to a fluid supply interface of a cell culture system.

Referring to FIGS. 1-11, a cap according to the invention for a cell culture container in accordance with the present device is generally designated by the reference numeral 1. FIG. 1 shows a perspective view of a preferred first embodiment of a cap 1 according to the invention, which comprises an essentially cylindrical cap housing 3 as its lateral surface, a connecting piece 5 facing away from the container and comprising a compensation opening 7 located on the lateral surface of, and a valve arrangement 9 arranged at the other end of connecting piece 5. Valve arrangement 9 comprises a magnetic ball-type valve, which will be explained in greater detail below with reference to the following figures. Compensation opening 7 in this embodiment is at least partially covered by a cover 11, which comprises several openings 13 and protects the membrane, if provided, lying underneath. Compensation opening 7 is arranged essentially on the circumferential or lateral surface of connecting piece 5. The diameter of cap housing 3 is dimensioned in such a way that connecting piece 5 and valve arrangement 9 do not project radially beyond the lateral surface of the housing. This offers the advantage that, when caps 1 are stored, the sensitive elements such as valve arrangement 9 and compensation opening 7 cannot be damaged or cannot suffer more than minimal damage when several caps 1 are stored together, in particular next to each other. In FIG. 1, it is also easy to see that valve arrangement 9 has a relatively small surface area, which means that the area to be cleaned when the fluid is to be changed is as small as possible.

FIG. 2 shows a cross-sectional view of the embodiment of cap 1 according to the invention of FIG. 1. In the embodiment illustrated here, the interior of cap housing 3 is not shown with a thread which would mate with a correspondingly threaded connector or extension of a cell culture container. It is obvious that, in addition to the standard threaded joints, it is also possible to use other methods to connect the cap and the container to each other such as a bayonet lock connection, a press-fit connection, a plug-in connection, or the like. Compensation opening 7 is equipped with both an (external) cover 11 and with a hydrophobic membrane 15, which enables an exchange of $CO_2$ (or other gases) between the interior of the cell culture container and the outer environment, especially during storage of the cell culture container.

Valve arrangement 9 comprises a connector or projection 19 at the end facing the container, the projection being connected to connecting piece 5, and a valve housing 17, which is arranged on the end of the connector facing away from the container. In the interior of valve housing 17 there is a magnetic element 21, and at the end of valve housing 17 facing away from the container, there is a valve seat 25, which comprises a shape which tapers down conically inward, so that a magnetic ball 23 can be arranged on valve seat 25 from the outside. In the embodiment shown here, valve seat 25 is made of a thermoplastic material. Examples of materials of this type include the thermoplastic elastomers (such as TPE), which are commercially available under the trade name Mediprene 500300M from Elasto or under the trade name Thermolast M TM4RST from Kraiburg TPE. It is obvious that the person skilled in the art can select similar plastic materials or composite materials with similar physical properties as an option.

In the embodiment shown here, magnetic element 21 is configured as a permanent magnet, wherein ferromagnetic materials are also suitable. Ball 23 is also made of magnetic material, i.e., in the form of a permanent magnet or as a ferromagnet, and it has a magnetic orientation which is opposite to the magnetic polarity of magnetic element 21, so that, in the normal state, i.e., in the state in which cap 1 is screwed onto or set into a cell culture container, ball 23 and magnetic element 21 attract each other and effectively block the valve opening in valve seat 25, so that no fluid can escape from the cell culture container or enter it from the outside.

It should be noted that, as a special embodiment, all of the elements of valve arrangement 9 with the exception of the magnetically configured components, i.e., magnetic element 21 and ball 23, can be integrated with the other portions of cap 1 to form a unit, as could be embodied, for example, by a single integral injection-molded part into which magnetic element 21 is installed from the inside and ball 23 from the outside.

Between connecting piece 5 and cap housing 3, a type of bellows element is arranged, which gives the elements arranged on connecting piece 5 a certain degree of flexibility relative to cap housing 3, wherein, however, a fluid-tight connection between connecting piece 5 and cap housing 3 is still guaranteed at all times. The bellows element does not interfere with the one-piece construction of cap housing 3 together with connecting piece 5. In other words, it is possible for cap 1 to be configured as an integral injection-molded part comprising cap housing 3, connecting piece 5, and the bellows element situated between them.

FIG. 3 shows a cross-sectional diagram of the preferred embodiment of cap 1 according to the invention described with reference to FIGS. 1 and 2. To avoid repetition, the elements are not described again here, and reference is made instead to the detailed description of FIG. 2.

FIG. 4 shows a perspective view of another embodiment of cap 1 according to the invention. The difference between this and the embodiment shown in FIGS. 1 to 3 is that compensation opening 7 is integrated essentially into the lateral surface of cylindrical connecting piece 5, openings 13 extending in the form of parallel slots in the circumferential direction over a predetermined angular distance of the circumference of connecting piece 5. Membrane 15 is, for example, arranged on the inner surface of connecting piece 5 in such a way that it covers openings 13 from the inside. A cover 11 like that present in the first embodiment is not provided in the embodiment of FIG. 4. All other elements of this second embodiment are identical to those of the elements of the first embodiment described on the basis of FIGS. 1 to 3.

FIG. 5 shows a perspective view of cap 1 according to the first embodiment, which has been screwed onto a cell culture container and is docked to a fluid supply interface of a cell culture system. Cap 1 is fastened by means of a thread on the interior of its cap housing 3 to a correspondingly threaded connector at the opening of the cell culture container in the known manner. On the side facing away from the container, valve arrangement 9 (not visible in FIG. 5) is docked to a corresponding coupling formation of a fluid supply interface 6 of a cell culture system. Fluid supply interface 6 comprises four coupling formations 8, to which corresponding supply containers for storing or holding fluids in the operating state of the cell culture system are connected. FIG. 5 does not show the control unit or the corresponding signaling means which control valve arrangement 9 without contact, that is, which in particular move the magnetic ball away from the valve seat of valve arrangement 9, so that a fluid flow path is opened up depending on the switching or control operation of fluid supply interface 6. The docking principle and the control function within the fluid supply interface are described in greater detail below with reference to FIGS. 10 and 11.

FIG. 6 shows a perspective view of a cell culture container with a cap 1 according to another embodiment of the present invention, in which a standard, commercially obtainable cell culture container 4 is equipped with a cap 1, which differs in one essential point from the previously described embodiments in that it comprises not just one but rather two valve arrangements 9. The two valve arrangements 9 are arranged in parallel to each other and extend in the axial direction from the essentially cylindrical connector piece 5, namely, on the end of cap 1 facing away from the container. Compensation opening 7 is arranged on the circumferential surface of connecting piece 5. Valve arrangements 9 are essentially identical in their configuration and are essentially symmetric with respect to the center point of the end surface, which is circular in this case, of connecting piece 5.

FIG. 7 shows a front view of cap 1 according to the second embodiment already illustrated in FIG. 6. It can be seen that the end surface of connecting piece 5 comprises not only two valve arrangements 9 but also two recesses 10, which are adapted to the automatic screwing-on or screwing-off of cap 1 and/or to the centering and thus aligning of cap 1 with respect to cell culture container 4. Recesses 10 are also adapted to the aligning of cap 1 with respect to fluid supply interface 6. It should be pointed out here that recesses 10 are not holes passing through the end surface of connecting piece 5 but rather are merely depressions of sufficient depth to allow the function described above to be realized.

It is obvious that, according to an aspect of the invention, there is no need to provide precisely two recesses 10 in the end surface; more than two or only one recess 10 can be present. In addition, the shape of recess 10 does not necessarily have to be circular. It can be rectangular, square, star-shaped, or polygonal or have some other shape.

FIG. 8 shows a cross-sectional view of a cap 1 according to the additional embodiment of the present invention illustrated in FIGS. 6 and 7. As previously explained, cap 1 comprises two valve arrangements 9 extending in the axial direction, aligned parallel to each other, and of essentially the same configuration. Their elements are identical to those described above in conjunction with the first preferred embodiment. For this reason, they are not described again here.

It can be seen that, instead of one fluid flow path through a docked cap 1, two possible fluid flow paths can be formed, depending on whether corresponding valve arrangements 9 are opened or not. It is obvious that two valve arrangements 9 of the embodiment shown in FIG. 8 can be controlled independently of each other. In particular, it is also possible that, when one of valve arrangements 9 is opened and a fluid is flowing through it, the other valve arrangement can be used as a pressure equalization opening to control the volume flow rate, i.e., its filling/emptying rate. Compensation opening 7 in the embodiment shown here is provided by membrane 15, which is arranged on the circumferential surface of connecting piece 5.

In contrast to the previously described embodiments, in this embodiment of cap 1, cap housing 3 is provided in its interior with threaded section 12, which mates with a correspondingly threaded section of the threaded connector of the cell culture container. It can also be seen in this embodiment that the radial dimension of connecting piece 5 provided with two valve arrangements 9 does not project beyond cap housing 3.

FIG. 9 shows a detail of a perspective, cross-sectional view of the cap shown in FIG. 6 with a cell culture container connected to it. As previously described with reference to FIG. 8, cap housing 3 of cap 1 comprises on its inside surface threaded section 12, which mates with a correspondingly threaded section of threaded connector 14 of cell culture container 4. FIG. 9 shows the completely screwed-on state of cap 1, wherein it can be seen that the open end of threaded connector 14 of cell culture container 4 butts up against the shoulder-like stop between cap housing 3 and connecting piece 5. Thus, cap 1 can be screwed firmly onto cell culture container 4, wherein the previously described stop stabilizes the connection even more effectively.

It is to be noted that the cap according to another aspect of the invention can also be used on cell culture containers which comprise more than one opening for the attachment of a cap. The primary advantage of the present invention, however, is that already existing cell culture containers can be equipped with an appropriate interface, so that already existing cell culture containers can be connected to an automated cell culture system.

It should also be noted that the cap according to another aspect of the invention, in particular the valve arrangement, can comprise a device which prevents elements of the valve arrangement such as the magnetic ball (in cases where a magnetic ball-type valve is being used) from being lost, especially in the undocked state. This device can be a type of plug-on or removable (grid-type) cage, preferably of plastic, which is set down onto the cap around the valve arrangement(s). It is conceivable that this cage could pivot automatically to the side when the cap is being docked to the fluid supply interface, or it could also be removed by hand.

With reference to FIGS. 10 and 11, the way in which cap 1 interacts with a fluid supply interface will now be explained briefly in greater detail.

On the right, FIG. 10 shows cap 1 according to the first embodiment described here; on the left is fluid supply interface 6, into which valve arrangement 9 of cap 1 is pushed. Valve arrangement 9 is pushed into empty space 18, namely, into the center area, so that magnetic ball 23 of valve arrangement 9 is still essentially free to move on valve seat 25. Valve arrangement 9 engages with fluid supply interface 6 by the contact established between the ring-shaped end surface of valve seat 25 and an opposing sealing surface 20 of fluid supply interface 6. As a result of this leak-tight contact between the ring-shaped end surface and opposing sealing surface 20, it is guaranteed that no fluid can escape from the fluid flow path. When valve arrangement 9 is opened, i.e., when ball 23 of valve arrangement 9 is no longer resting with a sealing action on valve seat 25, then a fluid flow path is created which extends from flow space 22 of fluid supply interface 6, past ball 23, and into the interior of cap 1, and thus, into the culture volume of cell culture container 4 (not shown in FIG. 10).

On the basis of FIG. 11, the interaction between valve arrangement 9, i.e., of cap 1, and fluid supply interface 6, which is controlled by control arrangement 24, will now be explained. Control arrangement 24 comprises a relaying arrangement 32 and a roller 28. Rotating roller 28 comprises an electric-motor drive (not shown in FIG. 11) for rotating the roller around its axis and a plurality of magnetic elements 30, which, in the exemplary embodiment shown here, are configured as permanent magnets. Magnetic elements 30 are preferably oriented in such a way that their N-S polarization direction coincides with a radius proceeding from the roller axis. Additional magnetic elements 30 can be arranged around the circumference of roller 28 at the axial positions of magnetic elements 30 shown in FIG. 11.

In the example shown, relaying arrangement 32 is provided between fluid supply interface 6 and roller 28 so that the valve arrangements 9 docked to fluid supply interface 6 can be switched with precision. For each possible valve arrangement 9, there is precisely one magnetic element 26—configured here as a permanent magnet—provided on the relaying arrangement 32. Each magnetic element 26 is arranged in a channel, wherein magnetic element 26 is supported movably between a position close to the roller and a position remote from the roller, i.e., a position closer to the valve arrangement.

Magnetic elements 26 are selected so that, at least when they are in the position remote from the roller, the magnetic field which they produce and which acts on ball 23 of associated valve arrangement 9 is stronger that the magnetic field which proceeds from magnetic element 21 on valve seat 25 and acts on ball 23. In addition, magnetic elements 26 are preferably arranged in accordance with their polarization along the axis of their movement, so that, for example, one pole such as the north pole points to the associated valve arrangement in the particular case and the opposite pole, here the south pole, points toward roller 28.

Relaying arrangement 32 is preferably arranged in such a way that magnetic elements 26 in the channels are preloaded by the force of gravity toward their position closer to roller, i.e., the position in which, by way of example, the two magnetic elements on the right in FIG. 11 are located.

If magnetic elements 30 are oriented appropriately, the approach of these magnetic elements 30 to magnetic elements 26 of relaying arrangement 32 will cause magnetic elements 26 to move away from their original position close to the roller into their position remote from the roller, i.e., closer to the valve arrangement, as a result of the magnetic fields proceeding from magnetic elements 30; this occurs when the magnets are oriented in the same way and the poles of the same polarity, i.e., the repelling poles, are facing each other. In similar fashion, when the opposite poles are facing each other, magnetic elements 30 and magnetic elements 26 attract each other and exert and an attractive force in addition to that of gravity.

When magnetic element 26 of relaying arrangement 32 approaches the associated valve arrangement, magnetic ball 23 is pulled more strongly by magnetic element 26 located in its position closer to the valve arrangement than by magnetic element 21 of its own valve arrangement 9. Ball 23 therefore moves out of its blocking position and into the open position, wherein the fluid passage through the valve arrangement is released. It can be seen that, when fluid supply interface 6 is in cleaning mode, essentially only the end surface facing away from the container must be cleaned, i.e., the area where ball 23 is arranged at the end of valve arrangement 9.

As an alternative to the embodiment of control unit 24 described above, it is also possible to use electromagnets as actuators to open and close the valves. Finally, it should also be mentioned that, instead of magnetic ball valves in the valve arrangement of the cap according to another aspect of the invention, piezoelectric valves could also be used or other valves known to the person skilled in the art which in particular are easy to clean at the end facing away from the container, so that contamination in the automated cell culture system can be avoided to the greatest extent possible.

With the subject matter described above, a cap for a cell culture container is provided, which can be used with standard, already existing cell culture containers, which can be produced at low cost, and which has a simple structure.

A wide variety of materials are available for the various parts discussed and illustrated herein. While the principles of this device have been described in connection with specific embodiments, it should be understood clearly that these descriptions are made only by way of example and are not intended to limit the scope of the device.

The invention claimed is:

1. A cap for a cell culture container for an automated cell-culture system, the container enclosing a culture volume and having an opening, the cap comprising:
 a valve arrangement suitable for filling the cell culture container with a fluid and/or for pumping fluid out from the cell culture container, the valve arrangement including a magnetic ball-type valve having (a) a magnetic element on a valve seat of conical or hemispherical configuration and (b) a ball of magnetic material for engagement/non-engagement with the valve seat, the magnetic element positioned toward the container and the ball positioned away from the container;
 a compensation opening suitable for aerating the cell culture container and/or for pressure compensation during filling or pumping out, the valve arrangement being designed to be switchable between an outlet position and a blocking position, to be connectable to a fluid supply interface, and to be switchable automatically; and
whereby the cap is configured for maintaining container closure in any orientation during filling, pumping out and cell propagation therein.

2. The cap according to claim 1 wherein the compensation opening is selectively configured as an opening which can be opened and closed and/or as a membrane.

3. The cap according to claim 1 wherein the valve arrangement and the opening of the cell culture container are arranged coaxially.

4. The cap according to claim 1 wherein the compensation opening is configured to be closed when the valve arrangement is not connected to the fluid supply interface and open when the valve arrangement is connected to the fluid supply interface.

5. The cap according to claim 1 wherein the cap is detachably connectable to the opening of the cell culture container by means of a threaded joint, a bayonet lock connection, a press-fit connection, a snap-on or plug-in connection, or a combination of these.

6. The cap according to claim 1 wherein the valve seat comprises a thermoplastic material such as a thermoplastic elastomer, silicone, or the like.

7. The cap according to claim 6 wherein the thermoplastic material has a Shore A hardness of approximately 25 to approximately 50.

8. The cap according to claim 1 wherein, with the exception of the valve arrangement, it is produced as a one-piece plastic unit by injection molding, and wherein the valve arrangement is attachable to it with a press fit.

9. The cap according to claim 8 wherein it is formed as a single-use/disposable article.

10. The cap according to claim 1 further including an additional valve arrangement serving as the compensation opening.

11. The cap according to claim 1 wherein a cell culture container encloses a culture volume and comprises an opening which includes the cap.

* * * * *